(12) United States Patent
Morikawa et al.

(10) Patent No.: US 11,053,180 B2
(45) Date of Patent: Jul. 6, 2021

(54) SEPARATION METHOD FOR HALOGENATED UNSATURATED CARBON COMPOUND

(71) Applicants: DAIKIN INDUSTRIES, LTD., Osaka (JP); KYOTO UNIVERSITY, Kyoto (JP)

(72) Inventors: Tatsuya Morikawa, Osaka (JP); Mana Shimokawa, Osaka (JP); Katsuki Fujiwara, Osaka (JP); Satoshi Tokuno, Osaka (JP); Masakazu Higuchi, Kyoto (JP); Susumu Kitagawa, Kyoto (JP)

(73) Assignees: DAIKIN INDUSTRIES, LTD., Osaka (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/845,834

(22) Filed: Apr. 10, 2020

(65) Prior Publication Data
US 2020/0239389 A1 Jul. 30, 2020

Related U.S. Application Data

(62) Division of application No. 15/748,362, filed as application No. PCT/JP2016/067831 on Jun. 15, 2016, now Pat. No. 10,654,775.

(30) Foreign Application Priority Data

Aug. 17, 2015 (JP) .................................. 2015-160401

(51) Int. Cl.
*C07C 7/12* (2006.01)
*B01D 53/02* (2006.01)
(Continued)

(52) U.S. Cl.
CPC ................ *C07C 7/12* (2013.01); *B01D 53/02* (2013.01); *B01J 20/226* (2013.01); *B01J 20/26* (2013.01);
(Continued)

(58) Field of Classification Search
CPC ......... C07C 7/12; C07C 21/18; C07C 21/158; C07C 17/398; C07C 11/04; C08G 79/14;
(Continued)

(56) References Cited

U.S. PATENT DOCUMENTS 2,917,556 A 12/1959 Percival
3,541,166 A 11/1970 Wada et al.
(Continued)

FOREIGN PATENT DOCUMENTS

CN 1833753 A 9/2006
JP 45-39082 B 12/1970
(Continued)

OTHER PUBLICATIONS

Extended European Search Report dated Mar. 21, 2019 issued by the European Patent Office in counterpart application No. 16836860.3.
(Continued)

*Primary Examiner* — Youngsul Jeong
(74) *Attorney, Agent, or Firm* — Sughrue Mion, PLLC

(57) ABSTRACT

The method according to this disclosure is a method for separating an unsaturated hydrocarbon having 2 or 3 carbon atoms and a halogenated unsaturated carbon compound formed by replacing at least one of hydrogen atoms included in the unsaturated hydrocarbon with a fluorine atom, from each other and is a method for selectively adsorbing either the unsaturated hydrocarbon or the halogenated unsaturated carbon compound by a porous coordination polymer that
(Continued)

includes a metallic ion having a valence of 2 to 4 and an aromatic anion having 1 to 6 aromatic ring(s).

6 Claims, 9 Drawing Sheets

(51) Int. Cl.
| | |
|---|---|
| *C07C 17/38* | (2006.01) |
| *C07C 11/04* | (2006.01) |
| *C07C 17/389* | (2006.01) |
| *C07C 21/185* | (2006.01) |
| *B01J 20/26* | (2006.01) |
| *B01J 20/28* | (2006.01) |
| *C07C 21/18* | (2006.01) |
| *C08G 79/14* | (2006.01) |
| *B01J 20/22* | (2006.01) |
| *C07C 65/03* | (2006.01) |
| *C07C 63/28* | (2006.01) |
| *C07C 63/307* | (2006.01) |
| *C07C 63/333* | (2006.01) |
| *C07F 15/04* | (2006.01) |
| *C07F 1/08* | (2006.01) |
| *C07F 7/00* | (2006.01) |
| *C07F 11/00* | (2006.01) |
| *B01J 20/02* | (2006.01) |

(52) U.S. Cl.
CPC ......... *B01J 20/28* (2013.01); *B01J 20/28066* (2013.01); *C07C 11/04* (2013.01); *C07C 17/389* (2013.01); *C07C 21/18* (2013.01); *C07C 21/185* (2013.01); *C08G 79/14* (2013.01); *B01J 20/0211* (2013.01); *B01J 20/0218* (2013.01); *B01J 20/0225* (2013.01); *B01J 20/0237* (2013.01); *C07C 63/28* (2013.01); *C07C 63/307* (2013.01); *C07C 63/333* (2013.01); *C07C 65/03* (2013.01); *C07F 1/08* (2013.01); *C07F 7/00* (2013.01); *C07F 11/00* (2013.01); *C07F 15/04* (2013.01)

(58) Field of Classification Search
CPC . B01J 20/28; B01J 20/26; B01J 20/22; B01D 53/02
See application file for complete search history.

(56) References Cited

U.S. PATENT DOCUMENTS

| | | |
|---|---|---|
| 5,345,013 A | 9/1994 | Van Bramer et al. |
| 5,866,727 A | 2/1999 | Van Bramer |
| 2006/0210458 A1 | 9/2006 | Mueller et al. |
| 2008/0190289 A1 | 8/2008 | Muller et al. |
| 2011/0172412 A1 | 7/2011 | Serre et al. |
| 2013/0283846 A1* | 10/2013 | Baumann ................ F25B 15/00 62/476 |
| 2014/0314606 A1 | 10/2014 | Maeyama et al. |

FOREIGN PATENT DOCUMENTS

| | | |
|---|---|---|
| JP | 48-24366 A | 7/1973 |
| JP | 51-076203 A | 7/1976 |
| JP | 51-105006 A | 9/1976 |
| JP | 52-122310 A | 10/1977 |
| JP | 53-018504 A | 2/1978 |
| JP | 55-111425 A | 8/1980 |
| JP | 08-511521 A | 12/1996 |
| JP | 11-222449 A | 8/1999 |
| JP | 2001-302551 A | 10/2001 |
| JP | 2004-161675 A | 6/2004 |
| JP | 2012-017268 A | 1/2012 |
| JP | 2012-228667 A | 11/2012 |
| JP | 2012228667 A * | 11/2012 ............. B01J 20/22 |
| JP | 2013-111563 A | 6/2013 |
| JP | 2013-184892 A | 9/2013 |
| JP | 2014-509359 A | 4/2014 |
| JP | 2014-211092 A | 11/2014 |
| JP | 2015-113336 A | 6/2015 |
| WO | 2011/045559 A1 | 4/2011 |
| WO | 2012/100094 A2 | 7/2012 |
| WO | 2014/028574 A2 | 2/2014 |

OTHER PUBLICATIONS

International Preliminary Report on Patentability with Translation of Written Opinion dated Mar. 1, 2018 in counterpart international application No. PCT/JP2016/067831.

International Search Report for PCT/JP2016/067831 dated Aug. 16, 2016 [PCT/ISA/210].

Communication dated Feb. 19, 2020 in counterpart EP Application No. 16 836 860.3.

* cited by examiner

SEPARATION METHOD FOR HALOGENATED UNSATURATED CARBON COMPOUND

CROSS-REFERENCE TO RELATED APPLICATIONS

This application is a Divisional of U.S. application Ser. No. 15/748,362, filed Jan. 29, 2018, which is a National Stage of International Application No. PCT/JP2016/067831 filed Jun. 15, 2016, claiming priority based on Japanese Patent Application No. 2015-160401 filed Aug. 17, 2015, the contents of all of which are incorporated herein by reference in their entirety.

TECHNICAL FIELD

The present invention relates to a separation method for a halogenated unsaturated carbon compound.

BACKGROUND ART

Halogenated unsaturated carbon compounds such as tetrafluoroethylene (TFE) are each widely used as a raw material of various types of chemical product such as a polymer material, and are extremely important industrial products for the industries. TFE is usually stored in a pressurized state. TFE is however highly unstable because TFE tends to polymerize, and special care needs to be taken for storage and transportation of TFE because TFE is explosive.

Various techniques have traditionally been developed to safely store and transport TFE. For example, Patent Document 1 describes methods for safely storing and safely transporting tetrafluoroethylene characterized in that tetrafluoroethylene is pressurized and dissolved into trifluoroethylene trichloride.

Patent Document 2 describes a method for stabilizing tetrafluoroethylene characterized in that perfluoroalkane having 1 to 5 carbon atom(s) is mixed with tetrafluoroethylene.

Patent Document 3 describes a method for transporting liquid tetrafluoroethylene in a container under pressure, and the method includes improvement including the fact that liquid carbon dioxide and the liquid tetrafluoroethylene are mixed with each other, and that carbon dioxide is present at an amount effective for preventing tetrafluoroethylene evaporated from the produced liquid mixture, from exploding at a temperature up to +25° C.

Patent Document 4 describes a shipping or storage container for long-term storage for tetrafluoroethylene, characterized in that the container includes tetrafluoroethylene in the form of a liquid mixture that includes tetrafluoroethylene and 35 to 65% by mol of hexafluoropropylene, and a gas space above the liquid mixture, and the gas space includes a mixture of vapors of tetrafluoroethylene and hexafluoropropylene from the liquid mixture.

PRIOR ART DOCUMENTS

Patent Documents

Patent Document 1: Japanese Patent Publication No. 45-39082

Patent Document 2: Japanese Laid-Open Patent Publication No. 55-111425

Patent Document 3: International Patent Publication No. 1996-511521

Patent Document 4: Japanese Laid-Open Patent Publication No. 11-222449

SUMMARY OF THE INVENTION

Problems to be Solved by the Invention

As described in Patent Documents 1 to 4, with the traditional techniques, it is necessary to stabilize TFE by adding an additive thereto to safely store and safely transport TFE, and TFE cannot alone be safely stored and transported. On the other hand, to use the halogenated unsaturated carbon compounds such as TFE each as a raw material of a polymer material or the like, the halogenated unsaturated carbon compound and impurities included in the halogenated unsaturated carbon compound need to be separated from each other. The separation of a halogenated unsaturated carbon compound and impurities included in the halogenated unsaturated carbon compound from each other has traditionally been generally conducted using distillation. A rectifying column having a very large number of stages has therefore been essential for the distillation, and a large amount of energy has been necessary for heating, cooling, and the like in the distillation.

An object of the present invention is to provide a method for highly efficiently separating a halogenated unsaturated carbon compound and impurities included therein from each other using a small amount of energy, a method for safely absorbing a halogenated unsaturated carbon compound, and a method for safely storing a halogenated unsaturated carbon compound.

Means for Solving Problems

Porous materials each having many pores therein such as activated carbon and zeolite have traditionally been used for various applications such as adsorption, deodorizing, and ion exchanging. A porous coordination polymer (PCP) has recently attracted attention as a new porous material. The PCP is also called as "metal-organic framework (MOF)" or "porous metallic complex". The PCP is a framework formed by integration of metallic complex molecules each constituted by a metallic ion and an organic ligand, and has a pore structure therein. It is considered that the PCP enables design and control of more uniform pores thereof compared to those of each of the traditional porous materials such as activated carbon and zeolite.

The present inventors found that a specific PCP was able to selectively adsorb either an unsaturated hydrocarbon or a halogenated unsaturated carbon compound and that a specific PCP was able to store a halogenated unsaturated carbon compound, and the present inventors completed the present invention. The present inventors further found that a specific PCP was able to selectively adsorb any one of a plurality of halogenated unsaturated carbon compounds whose molecular weights were different from each other.

According to a first aspect of the present invention, a method is provided for separating an unsaturated hydrocarbon having 2 or 3 carbon atoms and a halogenated unsaturated carbon compound having 2 or 3 carbon atoms from each other, wherein either the unsaturated hydrocarbon or the halogenated unsaturated carbon compound is selectively adsorbed to a porous coordination polymer that includes a metallic ion having a valence of 2 to 4 and an aromatic anion having 1 to 6 aromatic ring(s).

According to a second aspect of the present invention, a method is provided for adsorbing a halogenated unsaturated carbon compound having 2 or 3 carbon atoms by a porous coordination polymer that includes a metallic ion having a valence of 2 to 4 and an aromatic anion having 1 to 6 aromatic ring(s).

According to a third aspect of the present invention, a method is provided for storing a halogenated unsaturated carbon compound having 2 or 3 carbon atoms, wherein the storage is conducted by adsorbing the halogenated unsaturated carbon compound by a porous coordination polymer that includes a metallic ion having a valence of 2 to 4 and an aromatic anion having 1 to 6 aromatic ring(s).

According to a fourth aspect of the present invention, a porous coordination polymer comprising a halogenated unsaturated carbon compound having 2 or 3 carbon atoms stored therein is provided, wherein the porous coordination polymer includes a metallic ion having a valence of 2 to 4 and an aromatic anion having 1 to 6 aromatic ring(s).

According to a fifth aspect of the present invention, a method is provided for purifying a halogenated unsaturated carbon compound having 2 or 3 carbon atoms, the method comprising:

introducing a mixture including the halogenated unsaturated carbon compound and an unsaturated hydrocarbon having 2 or 3 carbon atoms into a porous coordination polymer that includes a metallic ion having a valence of 2 to 4 and an aromatic anion having 1 to 6 aromatic ring(s), selectively adsorbing either the unsaturated hydrocarbon or the halogenated unsaturated carbon compound to the porous coordination polymer, and taking out the other one of the unsaturated hydrocarbon and the halogenated unsaturated carbon compound.

According to a sixth aspect of the present invention, a method is provided for separating a plurality of halogenated unsaturated carbon compounds from each other that each have 2 or 3 carbon atoms and that are different from each other, wherein any one of the plurality of halogenated unsaturated carbon compounds is selectively adsorbed to a porous coordination polymer that includes a metallic ion having a valence of 2 to 4 and an aromatic anion having 1 to 6 aromatic ring(s).

According to a seventh aspect of the present invention, a method is provided for purifying a halogenated unsaturated carbon compound having 2 or 3 carbon atoms, the method comprising:

introducing a mixture including a plurality of halogenated unsaturated carbon compounds that are different from each other into a porous coordination polymer that includes a metallic ion having a valence of 2 to 4 and an aromatic anion having 1 to 6 aromatic ring(s), selectively adsorbing any one of the plurality of halogenated unsaturated carbon compounds to the porous coordination polymer, and taking out the other halogenated unsaturated carbon compound.

Effect of the Invention

According to the present invention, there can be provided a method for highly efficiently separating a halogenated unsaturated carbon compound and impurities included therein from each other, and a method for safely adsorbing and a method for storing the halogenated unsaturated carbon compound.

MODES FOR CARRYING OUT THE INVENTION

Figure 1:
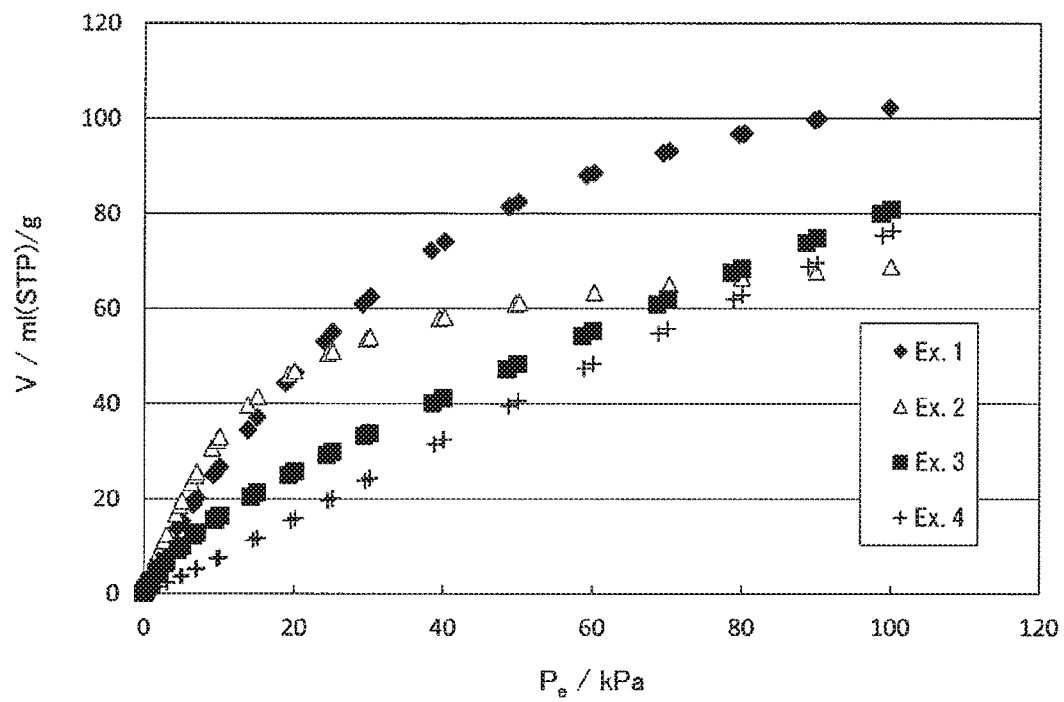
FIG. 1 is a graph of adsorption isotherms of tetrafluoroethylene at 298K of PCPs of Examples 1 to 4.
Figure 2A:
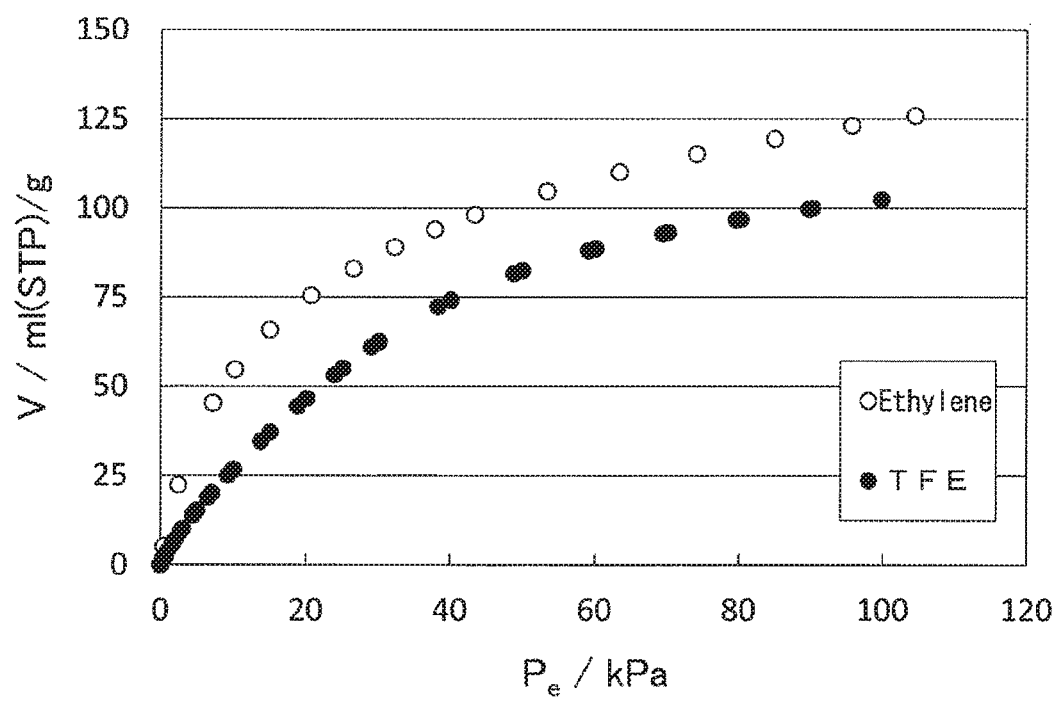
FIGS. 2A, 2B, 2C and 2D are graphs of adsorption isotherms of tetrafluoroethylene and ethylene at 298K of the PCPs of Examples 1 to 4.
Figure 2B:
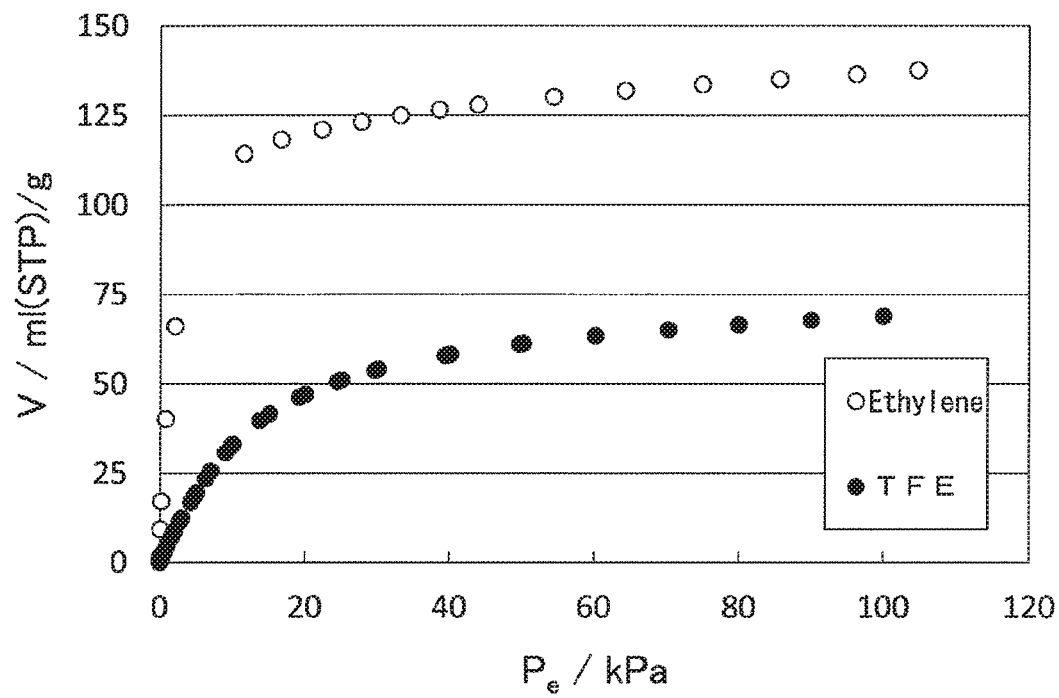
Figure 2C:
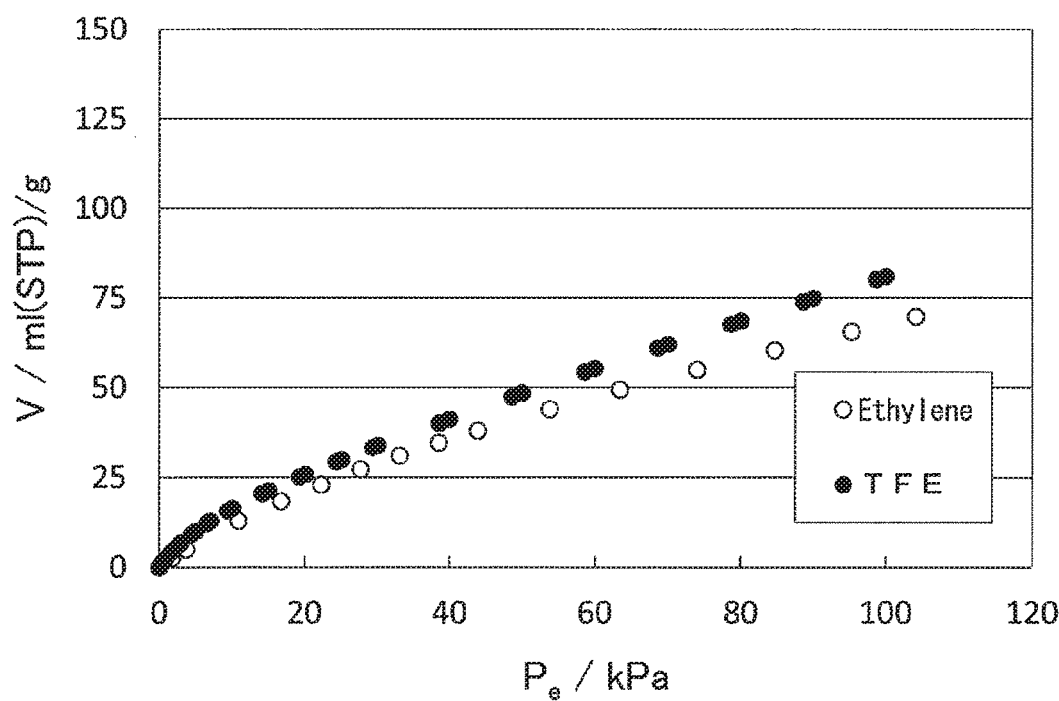
Figure 2D:
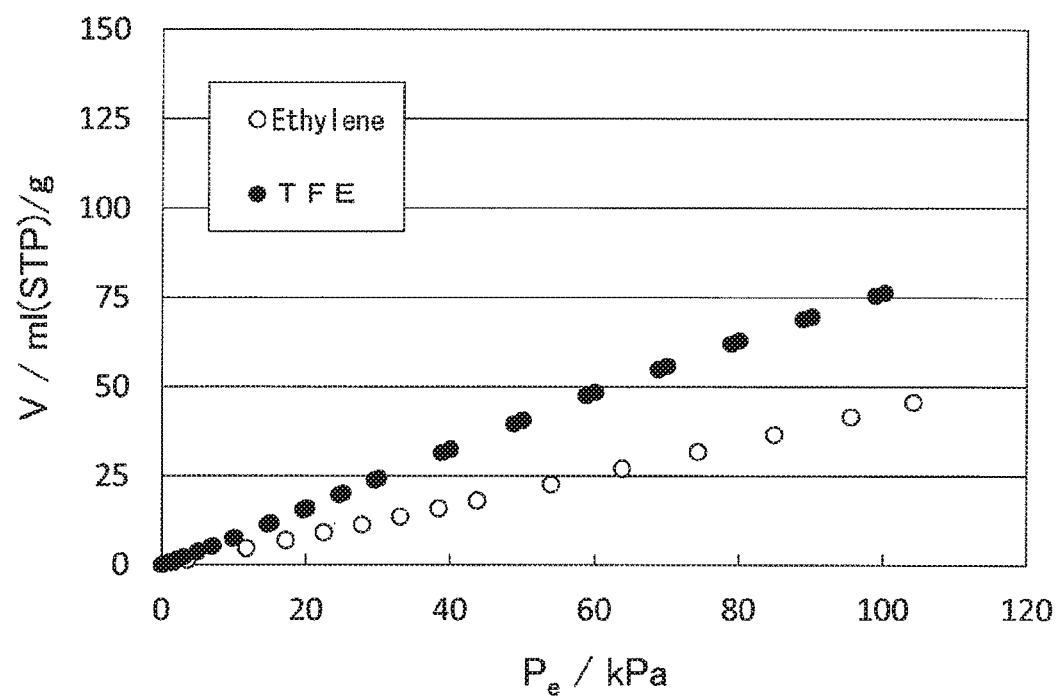

Embodiments of the present invention will be described below. The embodiments described below are each only an example and the present invention is not limited to the embodiments.

First Embodiment

This embodiment relates to a separation method for a halogenated unsaturated carbon compound according to the first aspect of the present invention. The separation method according to this embodiment is a method for separating an unsaturated hydrocarbon having 2 or 3 carbon atoms and a halogenated unsaturated carbon compound having 2 or 3 carbon atoms from each other, wherein either the unsaturated hydrocarbon or the halogenated unsaturated carbon compound is selectively adsorbed to a porous coordination polymer that includes a metallic ion having a valence of 2 to 4 and an aromatic anion having 1 to 6 aromatic ring(s). In the present specification, the "unsaturated hydrocarbon" means a hydrocarbon compound having a carbon backbone that includes at least one double bond between carbon atoms, the compound including no hetero atom. The unsaturated hydrocarbon may be, for example, ethylene, propylene, or the like. In the present specification, the "halogenated unsaturated carbon compound" means a carbon compound that has a carbon backbone including at least one double bond between carbon atoms, whose at least one carbon atom constituting the double bond between carbon atoms bonds with one or more halogen atom(s), the compound including no hetero atom. In this embodiment, the "halogenated unsaturated carbon compound" may be a halogenated unsaturated carbon compound formed by replacing one or more of hydrogen atom(s) included in the "unsaturated hydrocarbon" with a halogen atom. The halogen atom may be any one of fluorine, chlorine, bromine, and iodine. The halogenated unsaturated carbon compound may be, for example, difluoroethylene such as vinylidene fluoride, trifluoroethylene, tetrafluoriethylene, hexafluoropropylene, or the like.

The separation method for a halogenated unsaturated carbon compound according to this embodiment is not bound by any theory while it can be considered that the separation method is based on the mechanism described as follows. A PCP used in this embodiment has a porous structure having many pores formed therein. The PCP can take various structures in accordance with the combination of a metallic ion and a ligand that constitute the PCP. In a specific PCP, a metallic ion may be present on the surface of the pore and the pore surface may thereby have a positive charge thereon. On the other hand, the double bond between carbon atoms of the unsaturated hydrocarbon has a deviation ($\delta$−) of a negative charge. In contrast, the double bond between carbon atoms of the halogenated unsaturated carbon compound is bonded with a halogen atom that is an electron withdrawing group, and therefore has a smaller deviation ($\delta$−) of a negative charge or has a deviation ($\delta$+) of a positive charge. When the pore surface of the PCP has a positive charge thereon, the surface of the pore having the positive charge and the double bond of the unsaturated hydrocarbon that has the deviation of the negative charge interact with each other and the unsaturated hydrocarbon thereby tends to be adsorbed to the PCP. In contrast, because the double bond of the halogenated unsaturated carbon compound has the deviation of the positive charge, the halogenated unsaturated carbon compound is less likely to be adsorbed to the PCP compared to the unsaturated hydrocarbon. The halogenated unsaturated carbon compound and the unsaturated hydrocarbon can be separated from each other by using the fact that the PCP can selectively adsorb the unsaturated hydrocarbon as above. For example, when the pore surface of the PCP has a positive charge thereon, ethylene (an unsaturated hydrocarbon) tends to be adsorbed more significantly than tetrafluoroethylene (a halogenated unsaturated carbon compound) does. Tetrafluoroethylene and ethylene can be separated from each other by using the selective adsorption of ethylene as above. The selective adsorption by the PCP and the separation method using the selective adsorption by the PCP as above have not traditionally been known, and each achieve a surprising effect. In addition, the separation method using the PCP can be conducted in a highly-efficient manner using a small amount of energy and at a low pressure, compared to the traditional separation method using distillation.

Examples of the PCP that has a charge on the pore surface and that selectively adsorbs the unsaturated hydrocarbon include, for example, a PCP represented by a composition formula [$Cu_3(btc)_2$] (where btc is 1,3,5-benzenetricarboxylate) and a PCP represented by a composition formula [$Ni_2(dhtp)$] (where dhtp is 2,5-dihydroxyterephthalate). The details of the PCP usable in this embodiment will be described later.

Even in the case where the pore surface of the PCP has a positive charge thereon, when the size of the pore is relatively large, in the gas adsorption by the PCP, the contribution made thereto by the interaction conducted by the positive charge of the pore surface and the deviation of the negative charge of the double bond of the unsaturated hydrocarbon with each other as described above tends to be reduced. In this case, a substance having a higher boiling point tends to have a stronger interaction with the surface of the pore. The halogenated unsaturated carbon compound usually has a boiling point higher than that of the unsaturated hydrocarbon when their carbon backbones are the same. The halogenated unsaturated carbon compound therefore tends to be adsorbed to the PCP more significantly than the unsaturated hydrocarbon does when the size of the pore of the PCP is relatively large. The unsaturated hydrocarbon and the halogenated unsaturated carbon compound can be separated from each other also by using the selective adsorption of the halogenated unsaturated carbon compound as above. For example, tetrafluoroethylen tends to be adsorbed to the PCP more significantly than ethylene does because the tetrafluoroethylene has a boiling point (the boiling point: −76.3° C.) that is higher than that of ethylene (the boiling point: −104° C.). Tetrafluoroethylene and ethylene can be separated from each other by using the selective adsorption of tetrafluoroethylene as above.

Examples of the PCP that has relatively large pore diameter and that selectively adsorbs the halogenated unsaturated carbon compound as above include, for example, a PCP represented by a composition formula [$Cr_3O(OH)(bdc)_3$] (where bdc is 1,4-benzenedicarboxylate). The pore diameter of [$Cr_3O(OH)(bdc)_3$] is 2.7 nm and 3.4 nm, the pore diameter of [$Cu_3(btc)_2$] is 1.3 nm, and the pore diameter of [$Ni_2(dhtp)$] is 1.3 nm.

On the other hand, in a specific PCP, no metallic ion may be present on the surface of the pore and the pore surface may therefore have no charge thereon. In this case, a substance having a higher boiling point tends to have a stronger interaction with the pore surface. The halogenated unsaturated carbon compound has a boiling point higher than that of the unsaturated hydrocarbon as above when their carbon backbones are the same. The PCP therefore selectively adsorbs the halogenated unsaturated carbon compound compared to the unsaturated hydrocarbon when the pore surface of the PCP has no charge. The unsaturated hydrocarbon and the halogenated unsaturated carbon compound can be separated from each other also by using the selective adsorption of the halogenated unsaturated carbon compound as above.

Examples of the PCP whose pore surface has no charge thereon include, for example, a PCP represented by a composition formula [$Zr_6O_4(OH)_4(bpdc))_6$](where bpdc is 4,4'-biphenyldicarboxylate).

Each of the PCPs usable in this embodiment includes a metallic ion that has a valence of 2 to 4. Preferably, the metallic ion included in the PCP includes 2 or more positions at each of which a ligand can be coordinated and the metallic ion may be at least one selected from the group consisting of, for example, divalent metallic ions such as $Zn^{2+}$, $Cu^2$, $Mg^{2+}$, $Mn^{2+}$, $Fe^{2+}$, $Co^{2+}$, $Ni^{2+}$, and $Ti^{2+}$, trivalent metallic ions such as $Al^{3+}$, $Mn^{3+}$, $Fe^{3+}$, $Co^{3+}$, $Cr^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Y^{3+}$, and $Ga^{3+}$, and quadrivalent metallic ions such as $Mn^{4+}$, $Zr^{4+}$, and $Ti^{4+}$. In this embodiment, the PCP may include only one type of metallic ion or may include 2 or more metallic ions. The PCP can form an excellent porous framework by a coordination bond and an ionic bond since the PCP includes the metallic ion.

The PCP usable in this embodiment includes the aromatic anion having 1 to 6 aromatic ring(s) as a ligand. The aromatic anion included in the PCP is not especially limited and may be at least one selected from the group consisting of, for example, aromatic carboxylate anions such as a benzenedicarboxylate anion, a benzenetricarboxylate anion, a dioxidebenzenedicarboxylate anion, and a biphenyldicarboxylate anion. In this embodiment, the PCP may include only one type of aromatic anion or may include 2 or more types of aromatic anions. The PCP usable in this embodiment may include a ligand such as $O^{2-}$ or $OH^-$ in addition to the aromatic anions described above.

Examples of the PCP usable in this embodiment include, for example, $[Cu_3(btc)_2]$, $[Ni_2(dhtp)]$, $[Cr_3O(OH)(bdc)_3]$, $[Zr_6O_4(OH)_4(bpdc)_6]$, and a PCP represented by a composition formula $[Zr_6O_4(OH)_4(bdc)_6]$.

The PCP can be produced in accordance with any one of known and commonly used production methods. In particular, the PCP can be synthesized by, for example, mixing the metallic ion and the ligand with each other in a solvent and, depending on the case, heating and/or pressurizing the mixture. A microwave or an ultrasonic wave may be applied during the synthesis. Acetic acid may be added during the synthesis of the PCP. A PCP having high crystallizability and large pore surface area can be obtained by the addition of acetic acid. In this embodiment, the addition of acetic acid is not essential and acetic acid may properly be added in accordance with the purpose.

Preferably, a pretreatment is conducted for the PCP used in the method according to this embodiment before the use thereof to remove any solvent molecule and the like present in the pores thereof. The pretreatment may be conducted by, for example, drying the PCP at a temperature that is high to the extent that the PCP is not decomposed.

The structure of the PCP according to this embodiment can be identified using powder X-ray diffractometry (XRD). The weight of the solvent adsorbed inside the pores of the PCP can be measured by conducting thermogravimetric analysis (TG) for the PCP.

With the method according to this embodiment, in the case where the adsorption is conducted in a low pressure condition, the adsorption amount tends to be larger as the specific surface area of the PCP is smaller. Preferably, the specific surface area of the PCP is therefore small when the adsorption is conducted in a low pressure condition. The method according to this embodiment has an advantage that the separation of the halogenated unsaturated carbon compound such as TFE having explosive nature can more safely be conducted when the method is conducted in a low pressure condition. Preferably, for example, either the unsaturated hydrocarbon or the halogenated unsaturated carbon compound is selectively adsorbed to the PCP under the condition where the specific surface area of the PCP is 1,000 to 2,000 $m^2/g$ and where the adsorption gas pressure is 50 kPa (the absolute pressure) or lower. Examples of the PCP having the above specific surface area include, for example, $[Cu_3(btc)_2]$ (the specific surface area: 1,451 $m^2/g$) and $[Ni_2(dhtp)]$ (the specific surface area: 1,011 $m^2/g$).

The adsorption amount however reaches its saturation as the gas pressure of the adsorption gas becomes higher when the specific surface area of the PCP is small. In contrast, with the method according to this embodiment, in the case where the adsorption is conducted in a high pressure condition, the adsorption amount tends to be larger when the specific surface area of the PCP is larger. Preferably, the specific surface area of the PCP is therefore large when the adsorption is conducted in a high pressure condition. The method according to this embodiment has an advantage that the adsorption amount can further be increased and the separation of the halogenated unsaturated carbon compound can further efficiently be conducted when the method is conducted in a high pressure condition. Preferably, for example, either the unsaturated hydrocarbon or the halogenated unsaturated carbon compound is selectively adsorbed to the PCP under the condition where the specific surface area of the PCP is 2,000 to 3,000 $m^2/g$ and where the adsorption gas pressure is 50 to 250 kPa (the absolute pressure). Examples of the PCP having the above specific surface area include, for example, $[Cr_3O(OH)(bdc)_3]$ (the specific surface area: 2,996 $m^2/g$) and $[Zr_6O_4(OH)_4(bpdc)_4]$ (the specific surface area: 2,220 $m^2/g$).

The unsaturated hydrocarbon capable of being separated using the method according to this embodiment is not especially limited as long as the unsaturated hydrocarbon has 2 or 3 carbon atoms, and examples thereof include, for example, ethylene and propylene. Preferably, the unsaturated hydrocarbon capable of being separated using the method according to this embodiment is ethylene. The halogenated unsaturated carbon compound capable of being separated using the method according to this embodiment is not especially limited as long as the halogenated unsaturated carbon compound has 2 or 3 carbon atoms, and examples thereof include, for example, difluoroethylene such as vinylidene fluoride, trifluoroethylene, tetrafluoriethylene, and hexafluoropropylene. The halogenated unsaturated carbon compound may include one type of the compound alone or may also be a mixture that includes 2 or more types of the compound. Preferably, the halogenated unsaturated carbon compound capable of being separated using the method according to this embodiment is tetrafluoroethylene.

The separation method according to this embodiment can be conducted by, for example, causing a mixture gas including the unsaturated hydrocarbon and the halogenated unsaturated carbon compound to flow through an absorption tube filled with the PCP. Either the unsaturated hydrocarbon or the halogenated unsaturated carbon compound is selectively adsorbed to the PCP filled in the adsorption tube, and a gas having a concentration of the other gas higher than that of the mixture gas before passing through the adsorption tube can be obtained at the outlet of the adsorption tube, by conducting the method according to this embodiment in accordance with the above procedure.

Second Embodiment

This embodiment relates to an adsorption method for a halogenated unsaturated carbon compound according to the second aspect of the present invention. The adsorption method according to this embodiment is a method for adsorbing the halogenated unsaturated carbon compound having 2 or 3 carbon atoms to a porous coordination polymer that includes a metallic ion having a valence of 2 to 4 and an aromatic anion having 1 to 6 aromatic ring(s).

The PCPs usable in the first embodiment can also be used in this embodiment. The PCPs exemplified as the PCP capable of selectively adsorbing the unsaturated hydrocarbon in the first embodiment can also be advantageously used in the adsorption method for the halogenated unsaturated carbon compound according to this embodiment. With the method according to this embodiment, a larger amount of the halogenated unsaturated carbon compound can be adsorbed compared to the adsorption method using a traditional adsorbent such as activated carbon or zeolite. The method according to this embodiment has an advantage that the halogenated unsaturated carbon compound that is chemically unstable and has explosive nature such as tetrafluoroethylene can safely be adsorbed.

With the method according to this embodiment, in the case where the adsorption is conducted in a low pressure condition, the adsorption amount tends to be larger as the specific surface area of the PCP is smaller. Preferably, the specific surface area of the PCP is therefore small when the adsorption is conducted in a low pressure condition. With the method according to this embodiment, the adsorption of the halogenated unsaturated carbon compound having explosive nature such as TFE can more safely be conducted by conducting the method in a low pressure condition. Preferably, for example, the halogenated unsaturated carbon compound is adsorbed to the PCP under the condition where the specific surface area of the PCP is 1,000 to 2,000 $m^2/g$ and where the adsorption gas pressure is 100 kPa (the absolute pressure) or lower. Examples of the PCP having the above specific surface area include, for example, $[Cu_3(btc)_2]$ (the specific surface area: 1,451 $m^2/g$) and $[Ni_2(dhtp)]$ (the specific surface area: 1,011 $m^2/g$).

The adsorption amount however reaches its saturation as the gas pressure of the adsorption gas becomes higher when the specific surface area of the PCP is small. In contrast, with the method according to this embodiment, in the case where the adsorption is conducted in a high pressure condition, the adsorption amount tends to be larger when the specific surface area of the PCP is larger. Preferably, the specific surface area of the PCP is therefore large when the adsorption is conducted in a high pressure condition. With the method according to this embodiment, the adsorption amount can further be increased and the adsorption of the halogenated unsaturated carbon compound can further efficiently be conducted by conducting the method in a high pressure condition. Preferably, for example, the halogenated unsaturated carbon compound is adsorbed to the PCP under the condition where the specific surface area of the PCP is 2,000 to 3,000 $m^2/g$ and where the adsorption gas pressure is 100 to 800 kPa (the absolute pressure). Examples of the PCP having the above specific surface area include, for example, $[Cr_3O(OH)(bdc)_3]$(the specific surface area: 2,996 $m^2/g$) and $[Zr_6O_4(OH)_4(bpdc))_6]$(the specific surface area: 2,220 $m^2/g$).

The halogenated unsaturated carbon compound capable of being adsorbed using the method according to this embodiment is not especially limited as long as the halogenated unsaturated carbon compound has 2 or 3 carbon atoms, and examples thereof include, for example, difluoroethylene such as vinylidene fluoride, trifluoroethylene, tetrafluoriethylene, and hexafluoropropylene. The halogenated unsaturated carbon compound may include one type of the compound alone or may also be a mixture that includes 2 or more types of the compound. Preferably, the halogenated unsaturated carbon compound capable of being adsorbed using the method according to this embodiment is tetrafluoroethylene. With the adsorption method according to this embodiment, the halogenated unsaturated carbon compound can safely be adsorbed even when the halogenated unsaturated carbon compound is chemically unstable and is explosive, and no stabilizing agent needs to be added. The adsorption method according to this embodiment is therefore especially advantageous for adsorption of an explosive gas such as tetrafluoroethylene. With the adsorption method according to this embodiment, 25 to 35% by weight of the halogenated unsaturated carbon compound can be adsorbed relative to the total of the weight of the PCP and the weight of the halogenated unsaturated carbon compound.

The adsorption method according to this embodiment can be conducted by, for example, pressuring and filing the halogenated unsaturated carbon compound into a gas cylinder that is filled with the PCP. About a 25-fold or more adsorption amount can be achieved compared to that of the case where the halogenated unsaturated carbon compound is filled in the gas cylinder filled with no PCP, by conducting the method according to this embodiment in accordance with the above procedure.

Third Embodiment

This embodiment relates to a storage method for a halogenated unsaturated carbon compound according to the third aspect of the present invention. The storage method according to this embodiment is a method for storing a halogenated unsaturated carbon compound having 2 or 3 carbon atoms, wherein the storage is conducted by adsorbing the halogenated unsaturated carbon compound to a porous coordination polymer that includes a metallic ion having a valence of 2 to 4 and an aromatic anion having 1 to 6 aromatic ring(s). In this embodiment, the adsorption of the halogenated unsaturated carbon compound by the porous coordination polymer can be conducted using the adsorption method according to the second embodiment.

In the method according to this embodiment, the PCP usable in the first and the second embodiments can also be used. With the method according to this embodiment, a larger amount of the halogenated unsaturated carbon compound can be stored compared to the storage method that uses a traditional adsorbent such as activated carbon or zeolite. The method according to this embodiment has an advantage that the halogenated unsaturated carbon compound that is chemically unstable and has explosive nature such as tetrafluoroethylene can safely be stored.

The halogenated unsaturated carbon compound capable of being stored using the method according to this embodiment is not especially limited as long as the halogenated unsaturated carbon compound has 2 or 3 carbon atoms, and the halogenated unsaturated carbon compound capable of being adsorbed in the second embodiment can be stored. With the storage method according to this embodiment, the halogenated unsaturated carbon compound can safely be stored even when the halogenated unsaturated carbon compound is chemically unstable and has explosive nature, and no stabilizing agent needs to be added. The storage method according to this embodiment is therefore especially advantageous for storage of an explosive gas such as tetrafluoroethylene. With the storage method according to this embodiment, 25 to 35% by weight of the halogenated unsaturated carbon compound can be stored relative to the total of the weight of the PCP and the weight of the halogenated unsaturated carbon compound. The storage method according to this embodiment can be conducted by, for example, pressuring and filling the halogenated unsaturated carbon compound into a gas cylinder that is filled with the PCP. About a 25-fold or more storage amount can be achieved compared to that of the case where the halogenated unsaturated carbon compound is filled in the gas cylinder filled with no PCP, by conducting the method according to this embodiment in accordance with the above procedure.

Fourth Embodiment

This embodiment relates to a porous coordination polymer comprising a halogenated unsaturated carbon compound stored therein according to the fourth aspect of the present invention. The porous coordination polymer according to this embodiment is a porous coordination polymer that comprises a halogenated unsaturated carbon compound having 2 or 3 carbon atoms stored therein, and the porous coordination polymer is a porous coordination polymer that includes a metallic ion having a valence of 2 to 4 and an aromatic anion having 1 to 6 aromatic ring(s). The PCPs usable in the first to the third embodiments can also be used as the PCP according to this embodiment.

The halogenated unsaturated carbon compound stored in the PCP according to this embodiment is not especially limited as long as the halogenated unsaturated carbon compound has 2 or 3 carbon atoms, and examples thereof include, for example, difluoroethylene such as vinylidene fluoride, trifluoroethylene, tetrafluoriethylene, and hexafluoropropylene. The halogenated unsaturated carbon compound may include one type of the compound alone or may also be a mixture that includes 2 or more types of the compound. Preferably, the halogenated unsaturated carbon compound stored by the PCP according to this embodiment is tetrafluoroethylene. The PCP according to this embodiment can safely adsorb the halogenated unsaturated carbon compound even when the halogenated unsaturated carbon compound is chemically unstable and has explosive nature, and no stabilizing agent needs to be added. With the PCP according to this embodiment, the storage amount of the halogenated unsaturated carbon compound at a temperature of 298K and at an adsorption gas pressure of 100 kPa (the absolute pressure) can be 25 to 35% by weight relative to the total of the weight of the PCP and the weight of the halogenated unsaturated carbon compound. The PCP according to this embodiment can store a large amount of the halogenated unsaturated carbon compound in a low pressure condition, compared to the traditional absorbents such as activated carbon and zeolite.

Fifth Embodiment

This embodiment relates to a purification method for a halogenated unsaturated carbon compound according to the fifth aspect of the present invention. The method according to this embodiment is a method for purifying a halogenated unsaturated carbon compound having 2 or 3 carbon atoms. The method includes introducing a mixture including the halogenated unsaturated carbon compound having 2 or 3 carbon atoms and an unsaturated hydrocarbon having 2 or 3 carbon atoms into a porous coordination polymer that includes a metallic ion having a valence of 2 to 4 and an aromatic anion having 1 to 6 aromatic ring(s), selectively adsorbing either the unsaturated hydrocarbon or the halogenated unsaturated carbon compound to the porous coordination polymer, and taking out the other one of the unsaturated hydrocarbon and the halogenated unsaturated carbon compound.

The PCPs usable in the first embodiment can also be used in this embodiment. The halogenated unsaturated carbon compound may include an unsaturated hydrocarbon as an impurity. The PCP can selectively adsorb either the unsaturated hydrocarbon or the halogenated unsaturated carbon compound as above. When the unsaturated hydrocarbon is selectively adsorbed to the PCP, purified halogenated unsaturated carbon compound can be obtained using the above method. When the halogenated unsaturated carbon compound is selectively adsorbed to the PCP, purified halogenated unsaturated carbon compound can be obtained by taking out thereafter the halogenated unsaturated carbon compound from the PCP.

The method according to this embodiment can be conducted by, for example, causing a mixture gas including the unsaturated hydrocarbon and the halogenated unsaturated carbon compound to flow through an absorption tube filled with the PCP. When the mixture gas is caused to flow through the adsorption tube, either the unsaturated hydrocarbon or the halogenated unsaturated carbon compound is selectively adsorbed to the PCP filled in the adsorption tube, and the other one of the unsaturated hydrocarbon and the halogenated unsaturated carbon compound is taken out as a purified gas at the outlet of the absorption tube. When the halogenated unsaturated carbon compound is selectively adsorbed to the PCP, the halogenated unsaturated carbon compound can thereafter be taken out as a purified gas from the adsorption tube.

The halogenated unsaturated carbon compound capable of being purified using the method according to this embodiment is not especially limited as long as the halogenated unsaturated carbon compound has 2 or 3 carbon atoms, and may be the halogenated unsaturated carbon compound capable of being separated in the first embodiment. The unsaturated hydrocarbon that may be included as the impurity in the method according to this embodiment is not especially limited as long as the unsaturated hydrocarbon is an unsaturated hydrocarbon having 2 or 3 carbon atoms, and may be, for example, the unsaturated hydrocarbon capable of being separated in the first embodiment.

Purified vinylidene fluoride (VdF) can be obtained from a mixture including vinylidene fluoride and ethylene in accordance with a procedure described below as an example of the method according to this embodiment. In this example, for example, $[Cr_3O(OH)(bdc)_3]$ or $[Zr_6O_4(OH)_4(bpdc)_6]$ may be used as the PCP. When the mixture including vinylidene fluoride and ethylene is introduced into the PCP, vinylidene fluoride is selectively adsorbed to the PCP and ethylene to be the impurity is taken out. This is presumed to be caused by the fact that the boiling point of vinylidene fluoride ($-83°$ C.) is higher than the boiling point of ethylene ($-104°$ C.). Then, vinylidene fluoride is taken out from the PCP and purified vinylidene fluoride can thereby be obtained.

Purified trifluoroethylene can be obtained from a mixture including trifluoroethylene and ethylene in accordance with the same procedure as the above procedure. When the mixture including trifluoroethylene and ethylene is introduced into the PCP, trifluoroethylene is selectively adsorbed to the PCP, and ethylene to be the impurity is taken out. It is presumed to be caused by the fact that the boiling point of trifluoroethylene ($-51°$ C.) is higher than the boiling point of ethylene. Then, trifluoroethylene is taken out from the PCP and purified trifluoroethylene can thereby be obtained.

Sixth Embodiment

This embodiment relates to a separation method for a plurality of halogenated unsaturated carbon compounds that are different from each other, according to the sixth aspect of the present invention. The method according to this embodiment differs from that of the first embodiment for separating the halogenated unsaturated carbon compound and the unsaturated hydrocarbon from each other in that different types of halogenated unsaturated carbon compounds are separated from each other. The method according to this embodiment is a method for separating a plurality of halogenated unsaturated carbon compounds that each have 2 or 3 carbon atoms and that are different from each other, wherein any one of the plurality of halogenated unsaturated carbon compounds is selectively adsorbed to a porous coordination polymer that includes a metallic ion having a valence of 2 to 4 and an aromatic anion having 1 to 6 aromatic ring(s).

In this embodiment, the PCP usable in the first embodiment can also be used. The method according to this embodiment can separate the halogenated unsaturated carbon compounds from each other by selectively adsorbing to the PCP any one of the plurality of halogenated unsaturated carbon compounds whose types are different from each other. The mechanism enabling the separation of the halogenated unsaturated carbon compounds from each other by using the PCP is not bound by any theory while it is presumed that the mechanism is substantially what will be described as follows. As has been described in the first embodiment, it is considered that the tendency of the halogenated unsaturated carbon compound to be adsorbed to the PCP may vary in accordance with the presence or the absence of a charge on the pore surface of the PCP, the deviation of the charge of the halogenated unsaturated carbon compound, the boiling point of the halogenated unsaturated carbon compound, and the like. The halogenated unsaturated carbon compound differs in its physical properties such as the deviation of the charge and the boiling point depending on its type. It is considered that any one of the plurality of halogenated unsaturated carbon compounds whose types are different from each other can therefore be selectively adsorbed to the PCP.

The separation method according to this embodiment can conducted by, for example, causing a mixture gas including the plurality of halogenated unsaturated carbon compounds whose types are different from each other to flow through an absorption tube filled with the PCP. Any one of the halogenated unsaturated carbon compounds is selectively adsorbed to the PCP filled in the adsorption tube, and a gas having a concentration of the other halogenated unsaturated carbon compound higher than that in the mixture gas before passing through the adsorption tube is obtained at the outlet of the adsorption tube, by conducting the method according to this embodiment in accordance with the above procedure.

The halogenated unsaturated carbon compound capable of being separated using the method according to this embodiment is not especially limited as long as the halogenated unsaturated carbon compound has 2 or 3 carbon atoms, and, for example, the halogenated unsaturated carbon compounds each capable of being separated in the first embodiment can be separated from each other.

Vinylidene fluoride (VdF) and tetrafluoroethylene (TFE) can be separated from a mixture including vinylidene fluoride and tetrafluoroethylene in accordance with a procedure described below as an example of the method according to this embodiment. In this example, for example, $[Cr_3O(OH)(bdc)_3]$ or $[Zr_6O_4(OH)_4(bpdc))_6]$ may be used as the PCP. When the mixture including vinylidene fluoride and tetrafluoroethylene is introduced into the PCP, vinylidene fluoride is selectively adsorbed to the PCP, and vinylidene fluoride and tetrafluoroethylene are thereby separated from each other. $[Cr_3O(OH)(bdc)_3]$ and $[Zr_6O_4(OH)_4(bpdc))_6]$ each tend to selectively adsorb more significantly a substance having a higher boiling point as described above. The boiling point of vinylidene fluoride (−83° C.) is however lower than the boiling point of tetrafluoroethylene (−76.3° C.). Therefore, the selective adsorption of vinylidene fluoride by $[Cr_3O(OH)(bdc)_3]$ and $[Zr_6O_4(OH)_4(bpdc))_6]$ is surprising and considered as a singular adsorption phenomenon. Although the details of the mechanism of the selective adsorption of vinylidene fluoride by these PCPs are unknown, it is presumed to be caused by the fact that the deviation of the charge in VdF is asymmetric while the deviation of the charge in TFE is symmetric.

Trifluoroethylene and tetrafluoroethylene can be separated from a mixture including trifluoroethylene and tetrafluoroethylene in accordance with the same procedure as the above procedure. When the mixture including trifluoroethylene and tetrafluoroethylene is introduced into the PCP, trifluoroethylene is selectively adsorbed to the PCP and trifluoroethylene and tetrafluoroethylene are thereby separated from each other. The selective adsorption of trifluoroethylene is presumed to be caused by the facts that the deviation of the charge in trifluoroethylene is asymmetric and that the boiling point of trifluoroethylene (−51° C.) is higher than the boiling point of tetrafluoroethylene.

Seventh Embodiment

This embodiment relates to a purification method for a halogenated unsaturated carbon compound according to the seventh aspect of the present invention. The method according to this embodiment differs from that of the fifth embodiment for removing the unsaturated hydrocarbon as an impurity in that a halogenated unsaturated carbon compound of a type different from that of halogenated unsaturated carbon compound to be purified is removed as an impurity. The method according to this embodiment is a method for purifying a halogenated unsaturated carbon compound having 2 or 3 carbon atoms. The method includes introducing a mixture including a plurality of halogenated unsaturated carbon compounds whose types are different from each other into a porous coordination polymer including a metallic ion having a valence of 2 to 4 and an aromatic anion having 1 to 6 aromatic ring(s), selectively adsorbing any one of the plurality of halogenated unsaturated carbon compounds to the porous coordination polymer, and taking out the other halogenated unsaturated carbon compound.

In this embodiment, the PCPs usable in the first embodiment can also be used. The halogenated unsaturated carbon compound may include a halogenated unsaturated carbon compound whose type is different from the former. As described above, the PCP can selectively adsorb any one of the plurality of halogenated unsaturated carbon compounds each different from each other. When the halogenated unsaturated carbon compound to be the impurity is selectively adsorbed to the PCP, a targeted purified halogenated unsaturated carbon compound can be obtained using the above method. When the targeted halogenated unsaturated carbon compound is selectively adsorbed to the PCP, the targeted purified halogenated unsaturated carbon compound can be obtained by thereafter taking out the halogenated unsaturated carbon compound from the PCP.

The method according to this embodiment can be conducted by, for example, causing a mixture gas including the plurality of halogenated unsaturated carbon compounds each different from each other to flow through an absorption tube filled with the PCP. When the mixture gas is caused to flow through the adsorption tube, any one of the halogenated unsaturated carbon compounds is selectively adsorbed to the PCP filled in the adsorption tube and the other halogenated unsaturated carbon compound is taken out as a purified gas at the outlet of the adsorption tube. When the targeted halogenated unsaturated carbon compound is selectively adsorbed to the PCP, the targeted halogenated unsaturated carbon compound can thereafter be taken out from the adsorption tube as a purified gas.

The halogenated unsaturated carbon compound capable of being purified using the method according to this embodiment and the halogenated unsaturated carbon compound that may be included as the impurity are not especially limited as long as both of the halogenated unsaturated carbon compounds has 2 or 3 carbon atoms and, for example, may be the halogenated unsaturated carbon compound capable of being separated in the first embodiment.

Purified tetrafluoroethylene can be obtained from a mixture including vinylidene fluoride (VdF) and tetrafluoroethylene (TFE) in accordance with a procedure described below as an example of the method according to this embodiment. In this example, for example, $[Cr_3O(OH)(bdc)_3]$ or $[Zr_6O_4(OH)_4(bpdc)_6]$ may be used as the PCP. When the mixture including vinylidene fluoride and tetrafluoroethylene is introduced into the PCP, vinylidene fluoride is selectively adsorbed to the PCP and purified tetrafluoroethylene is taken out. The mechanism of selective adsorption of vinylidene fluoride by the PCP is as described above. Vinylidene fluoride adsorbed to the PCP is thereafter taken out and purified vinylidene fluoride can thereby be obtained.

Purified tetrafluoroethylene can be obtained from a mixture including trifluoroethylene and tetrafluoroethylene (TFE) by selectively adsorbing trifluoroethylene to the PCP in accordance with a same procedure. Trifluoroethylene adsorbed to the PCP is thereafter taken out and purified trifluoroethylene can thereby be obtained.

EXAMPLES

Examples of the present invention will be described below while the present invention is not limited to Examples below.

Example 1

$[Cu_3(btc)_2]$ was prepared in accordance with the following procedure as a PCP for Example 1. 57.6 mL of a 50%-by-volume ethanol aqueous solution was added to 2.11 g of copper (II) nitrate trihydrate and 1.01 g of 1,3,5-benzenetri(methyl carboxylate) to be stirred for 10 minutes and a microwave was applied to this mixture to react this mixture at 140° C. for 60 minutes. A solid was collected by suction filtration and ethanol was added thereto to conduct ultrasonic washing. After the washing, the solid collected by the suction filtration was dried in a vacuum to obtain 1.24 g of the PCP for Example 1.

Example 2

$[Ni_2(dhtp)]$ was prepared in accordance with the following procedure as a PCP for Example 2. 72 mL of N,N-dimethylformamide and 3.6 mL of water were added to 3.63 g of nickel (II) nitrate hexahydrate and 0.72 g of 2,5-dihydroxyterephthalic acid and an ultrasonic wave was applied to this mixture for dissolution. The obtained solution was reacted in an autoclave at 110° C. for 21.5 hours. A solid was collected by suction filtration and was dried in a vacuum to obtain a solid of 2.44 g. This solid was washed with ethanol and a solid collected thereafter by suction filtration is dried in a vacuum to obtain 1.91 g of the PCP for Example 2.

Example 3

$[Cr_3O(OH)(bdc)_3]$ was prepared in accordance with the following procedure as a PCP for Example 3. 50 mL of water was added to 2.97 g of chromium (III) chloride hexahydrate and 1.85 g of terephthalic acid to be stirred and this mixture was reacted in an autoclave at 210° C. for 6 hours. After centrifugal separation, the supernatant solution was removed and the rest was dried in a vacuum. A solid was obtained, and N,N-dimethylformamide was added to the solid to conduct ultrasonic washing. Then, the supernatant solution was removed. Ethanol was added to the rest to conduct ultrasonic washing, and then the supernatant was removed. The rest was dried in a vacuum to obtain 1.59 g of the PCP for Example 3.

Example 4

$[Zr_6O_4(OH)_4(bpdc))_6]$ was prepared in accordance with the following procedure as a PCP for Example 4. $[Zr_6O_4(OH)_4(bpdc))_6]$ for Example 4 was a substance to which acetic acid was added during its synthesis (hereinafter, also referred to as "$[Zr_6O_4(OH)_4(bpdc)_6]$+AcOH"). 50 mL of N,N-dimethylformamide, 100 μg of water, and 6.86 mL of acetic acid were added to 0.93 g of zirconium (IV) chloride and 0.98 g of 4,4'-biphenyldicarboxylic acid while stirring. The obtained solution was reacted in an autoclave at 120° C. for 48 hours. N,N-dimethylformamide was added to the resultant content and then a solid was collected by suction filtration. The collected solid was dried in a vacuum to obtain 2.06 g of the PCP for Example 4.

(Measurement of Specific Surface Area)

For each of the PCPs for Examples 1 to 4 that were prepared as described above and for which a pretreatment was conducted, measurement of the specific surface area was conducted. The specific surface area was measured using an automatic specific surface area/pore distribution measuring apparatus "BEL SORP-mini II" manufactured by MicrotrackBel Corp., and was calculated using a BET method. The results are shown in Table 1 below.

TABLE 1

| | Abbreviated Name | Specific Surface Area ($m^2/g$) |
|---|---|---|
| Example 1 | $[Cu_3(btc)_2]$ | 1,451 |
| Example 2 | $[Ni_2(dhtp)]$ | 1,011 |
| Example 3 | $[Cr_3O(OH)(bdc)_3]$ | 2,996 |
| Example 4 | $[Zr_6O_4(OH)_4(bpdc)_6]$ + AcOH | 2,220 |

(Measurement of Adsorption Amount)

For each of the PCPs for Examples 1 to 4 for which the pretreatment was conducted as described above, measurement of the adsorption amounts of ethylene and TFE was conducted. Either of two types of apparatus shown in Table 2 was used as the adsorption amount measuring apparatus in accordance with the pressure range for the measurement.

TABLE 2

| | Name | Pressure Range for Measurement |
|---|---|---|
| Apparatus 1 | High precision gas/vapor adsorption amount measuring apparatus "BEL SORP-max" manufactured by MicrotrackBel Corp., | 0.4 Pa to 100 kPa |
| Apparatus 2 | High pressure gas adsorption amount measuring apparatus "BEL SORP-HP" manufactured by MicrotrackBel Corp., | 1 kPa to 1 MPa |

FIG. 1 shows adsorption isotherms obtained by measuring the adsorption amounts of TFE at 298K for the PCPs of Examples 1 to 4. It can be seen from FIG. 1 that the TFE adsorption amount in the PCP of Example 1 was the largest. It can also be seen that, when the gas pressure of the TFE gas was 80 kPa or lower, the adsorption amount of TFE in the PCP of Example 2 was larger than the adsorption amount of TFE in each of the PCPs of Examples 3 and 4. On the other hand, when the gas pressure of the TFE gas exceeded 80 kPa, the adsorption amounts of TFE in the PCPs of Examples 3 and 4 were each larger than the adsorption amount of TFE in the PCP of Example 2.

FIGS. 2A, 2B, 2C and 2D respectively show adsorption isotherms obtained by measuring the adsorption amounts of ethylene and TFE at 298K for the PCPs of Example 1, Example 2, Example 3, and Example 4. It can be seen from FIGS. 2A and 2B that the PCPs of Example 1 and Example 2 selectively adsorbed ethylene more significantly than TFE. It can also be seen for the PCPs of Example 1 and Example 2 that the adsorption amounts of TFE approached their saturation amounts as the adsorption gas pressures approached 100 kPa under a temperature condition of 298K. On the other hand, it can be seen from FIGS. 2C and 2D that the PCPs of Examples 3 and 4 selectively adsorbed TFE more significantly than ethylene. It can also be seen for the PCPs of Examples 3 and 4 that the adsorption amounts of ethylene and TFE was increased as the adsorption gas pressure was increased in a pressure range of 100 kPa or lower.

Figure 3A:
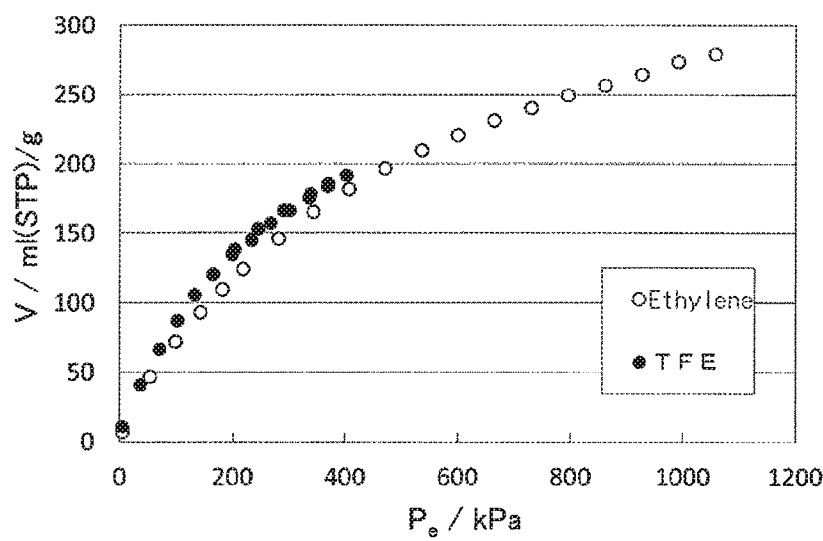
FIGS. 3A and 3B are graphs of adsorption isotherms of tetrafluoroethylene and ethylene at 298K of the PCPs of Examples 3 and 4.
Figure 3B:
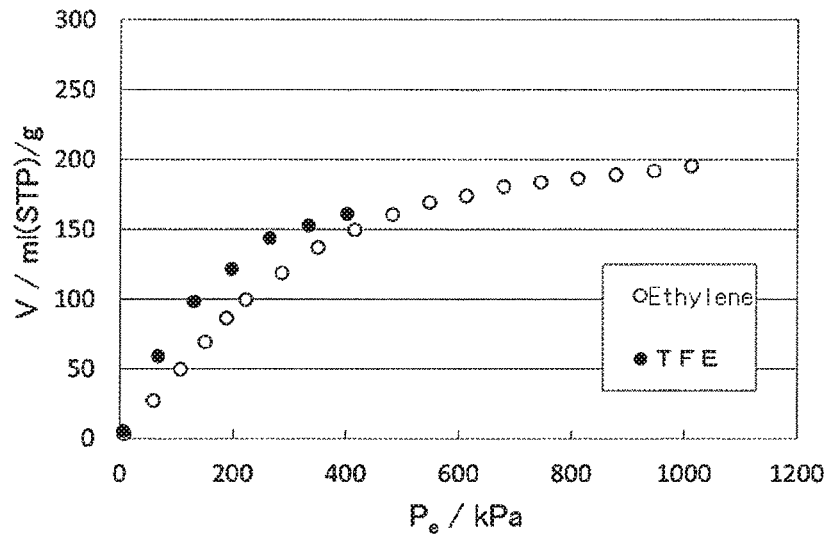

FIGS. 3A and 3B respectively show adsorption isotherms obtained by measuring the adsorption amounts of ethylene and TFE at 298K for the PCPs of Examples 3 and 4. It can be seen from FIGS. 3A and 3B that the adsorption amounts of TFE approached their saturation amounts as the adsorption gas pressure approached 400 kPa under the temperature condition of 298K for the PCPs of Examples 3 and 4.

Figure 4:
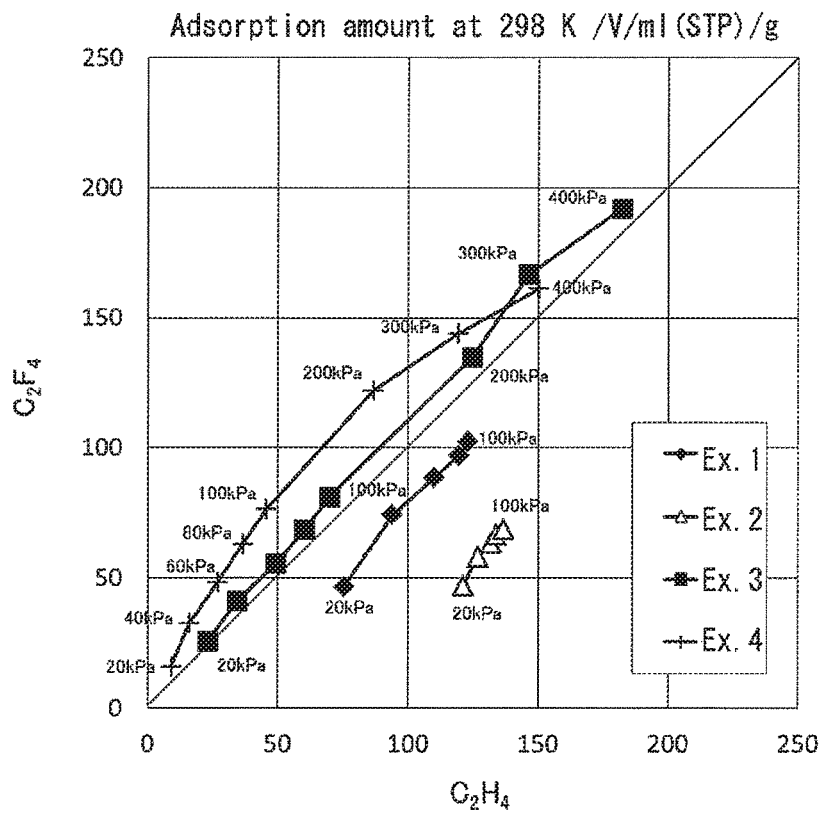
FIG. 4 is a graph showing the selectivity of gas adsorption by the PCPs of Examples 1 to 4.

FIG. 4 is a graph showing the selectivity of the gas adsorption by the PCPs of Examples 1 to 4 at a temperature of 298K. As shown in FIG. 4, the PCPs of Examples 1 and 2 selectively adsorbed ethylene. This was considered to be caused by the fact that the positive charge of the metallic ion present on the pore surface of the PCP and the deviation (δ−) of the negative charge of the double bond of ethylene interacted with each other. On the other hand, the PCP of Example 3 selectively adsorbed TFE. This was considered to be caused by the fact that the pore diameter of the PCP of Example 3 was relatively large and thus TFE having a boiling point (the boiling point: −76.3° C.) higher than that of ethylene (the boiling point: −104° C.) was selectively adsorbed. It was confirmed from the above results that all of the PCPs of Examples 1 to 4 were usable for separating ethylene and TFE from each other. The PCP of Example 4 also selectively adsorbed TFE. This was considered to be caused by the fact that the pore surface of the PCP of Example 2 had no charge thereof and thus TFE having the higher boiling point than that of ethylene was selectively adsorbed.

Figure 5A:
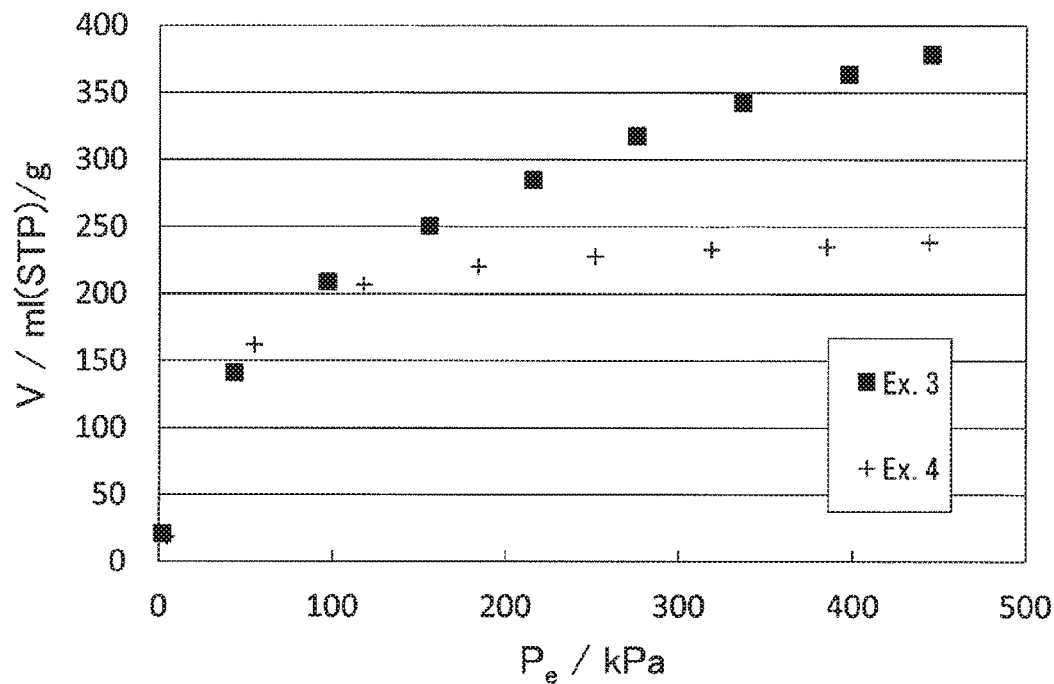
FIGS. 5A, 5B and 5C are graphs of adsorption isotherms of tetrafluoroethylene at 260K, 273K, and 298K of the PCPs of Examples 3 and 4.
Figure 5B:
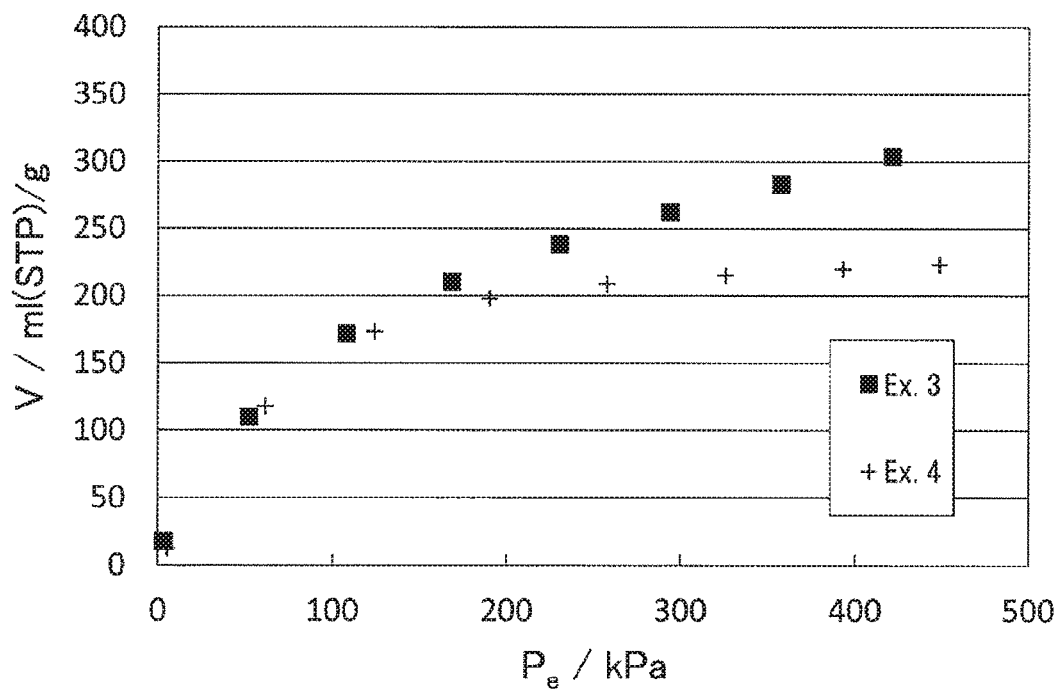
Figure 5C:
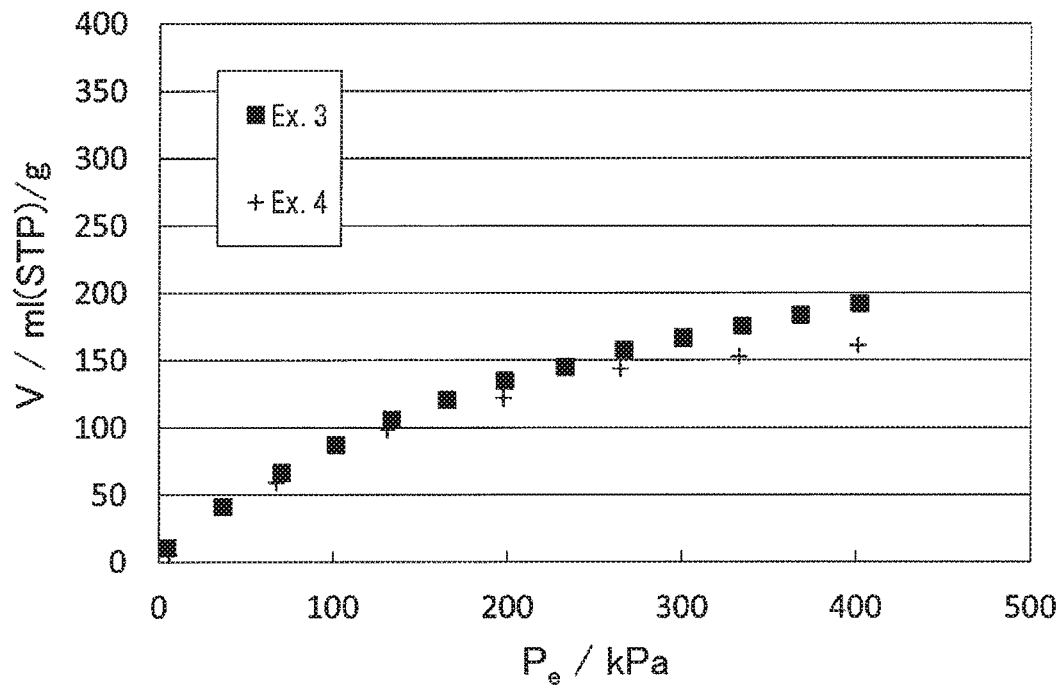

FIGS. 5A, 5B and 5C respectively show adsorption isotherms obtained by measuring the adsorption amounts of TFE at 260K, 273K, and 298K for the PCPs of Examples 3 and 4. It can be seen from FIGS. 5A to 5C that, for both of the PCPs of Examples 3 and 4, the adsorption amounts of TFE were increased as the adsorption gas pressure was increased and the adsorption amounts of TFE were increased as the temperature was decreased. The adsorption amount of TFE in the PCP of Example 3 was larger than the adsorption amount of TFE in the PCP of Example 4 and the difference therebetween was more remarkable as the temperature was lower.

Figure 6:
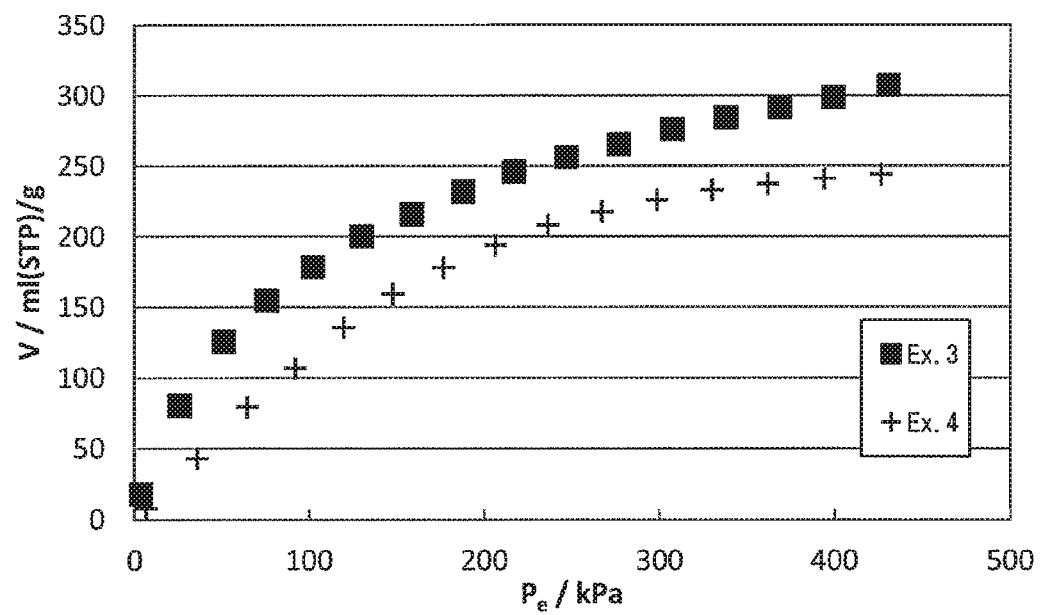
FIG. 6 is a graph of adsorption isotherms of vinylidene fluoride at 298K of the PCPs of Examples 3 and 4.

For each of the PCPs of Example 3 and Example 4, measurement of the adsorption amount of vinylidene fluoride (VdF) was conducted. Either of the two types of apparatus shown in Table 2 was used in accordance with the pressure range for the measurement as the adsorption amount measuring apparatus. FIG. 6 shows adsorption isotherms obtained by measuring the adsorption amounts of VdF at 298K for the PCPs of Examples 3 and 4. It can be seen from FIG. 6 that, for the PCP of Example 3, the adsorption amount of VdF was increased as the adsorption gas pressure was increased in a pressure range of 400 kPa or lower under a temperature condition of 298K. It can also be seen from FIG. 6 that, for the PCP of Example 4, the adsorption amount of VdF was increased as the adsorption gas pressure was increased and the adsorption amount of VdF approached its saturation amount as the adsorption gas pressure approaches 400 kPa, under a temperature condition of 298K.

Figure 7:
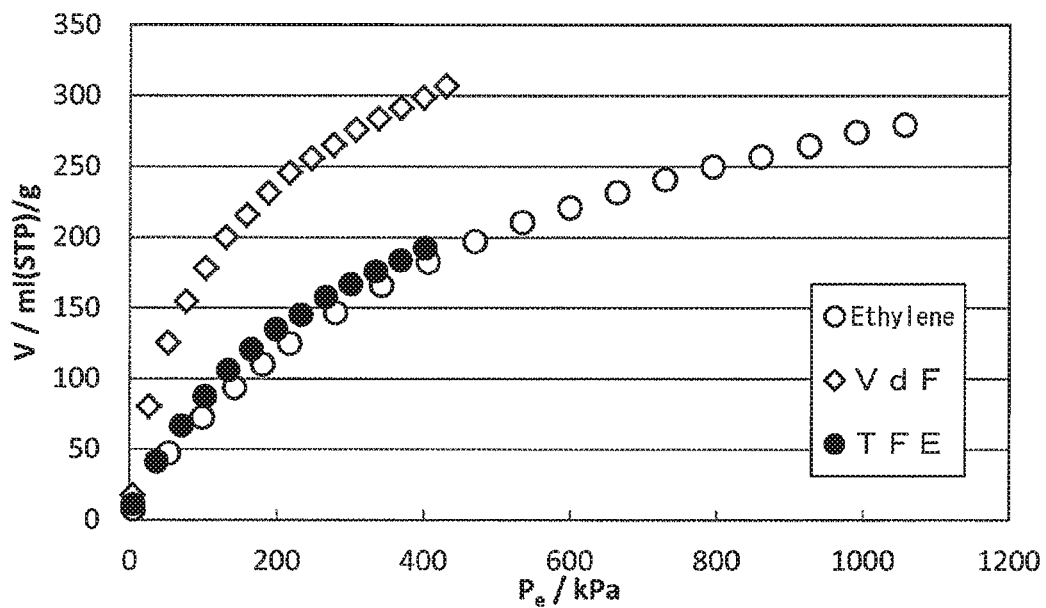
FIG. 7 is a graph of adsorption isotherms of vinylidene fluoride, tetrafluoroethylene, and ethylene at 298K of the PCP of Example 3.
Figure 8:
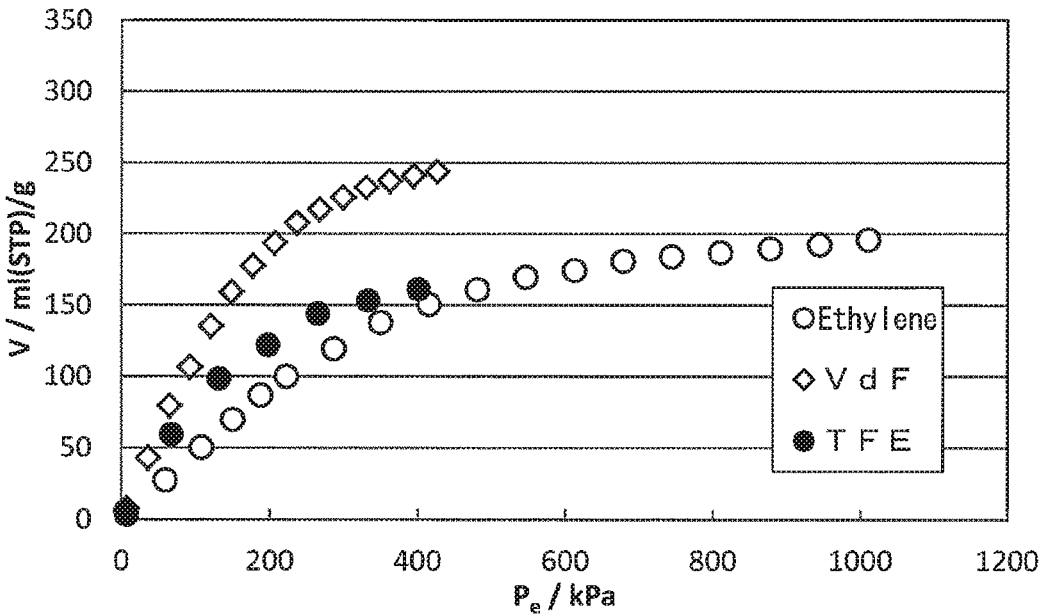
FIG. 8 is a graph of adsorption isotherms of vinylidene fluoride, tetrafluoroethylene, and ethylene at 298K of the PCP of Example 4.

FIG. 7 shows adsorption isotherms obtained by respectively measuring the adsorption amounts of VdF, ethylene, and TFE at 298K for the PCP of Example 3. FIG. 8 shows adsorption isotherms obtained by respectively measuring the adsorption amounts of VdF, ethylene, and TFE at 298K for the PCP of Example 4. As shown in FIG. 7 and FIG. 8, for both of the PCPs of Example 3 and Example 4, the adsorption amount of VdF also presented the largest value compared to the adsorption of ethylene and TFE.

Figure 9:
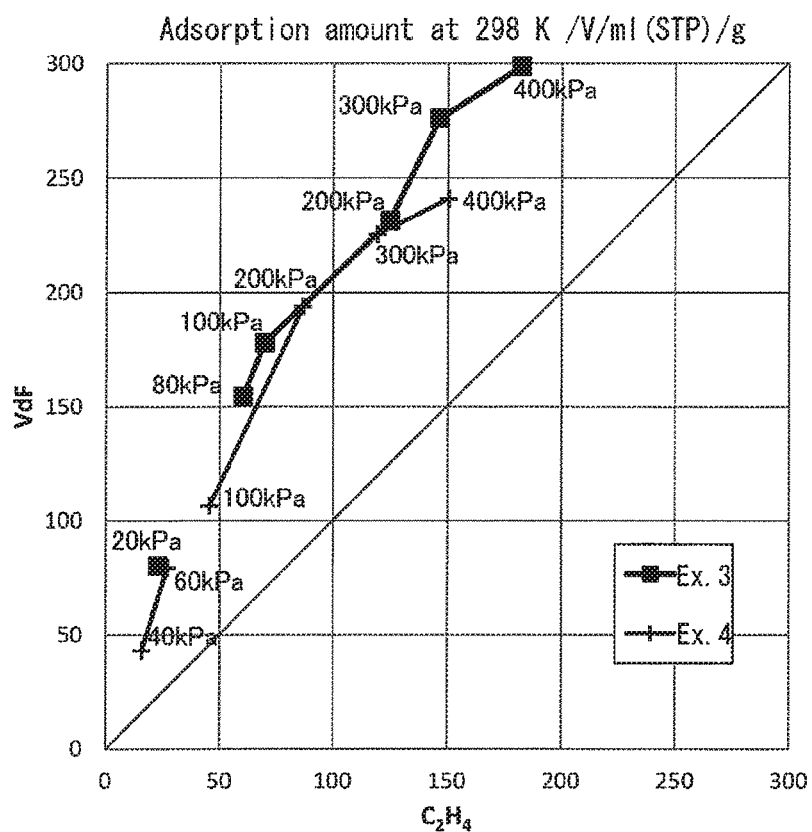
FIG. 9 is a graph showing the selectivity of gas adsorption between vinylidene fluoride and ethylene by the PCPs of Examples 3 and 4.
Figure 10:
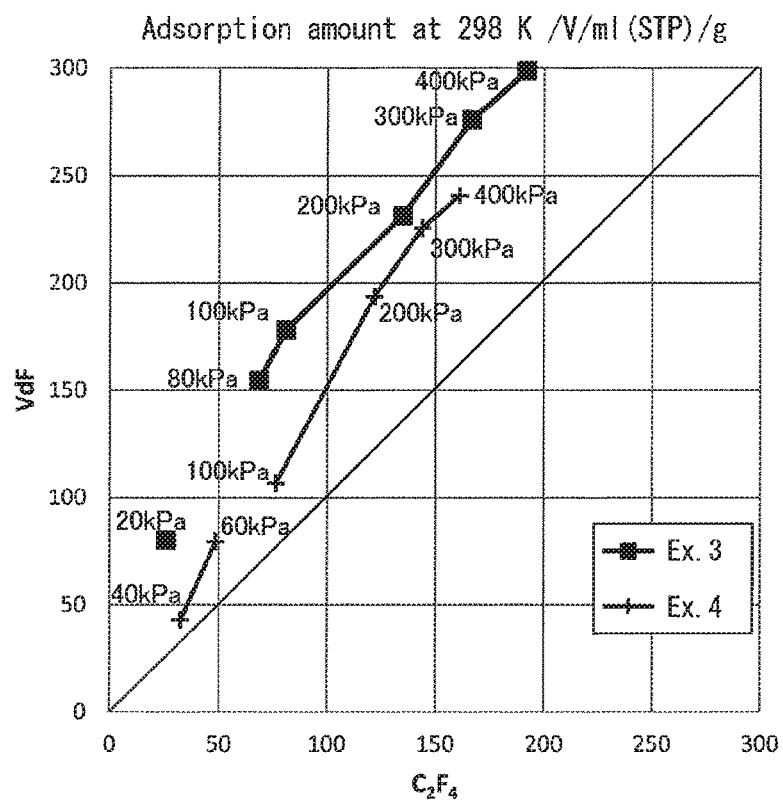
FIG. 10 is a graph showing the selectivity of gas adsorption between vinylidene fluoride and tetrafluoroethylene by the PCPs of Examples 3 and 4.

FIG. 9 and FIG. 10 are graphs showing the selectivity of the gas adsorption by the PCPs of Examples 3 and 4 at a temperature of 298K. FIG. 9 shows the selectivity of the gas adsorption for VdF and ethylene thereby, and FIG. 10 shows the selectivity of the gas adsorption for VdF and TFE thereby. As shown in FIG. 9, the PCPs of Example 3 and Example 4 each selectively adsorbed VdF compared to ethylene. This was presumed to be caused by the fact that the boiling point of the VdF (−83° C.) was higher than the boiling point of ethylene (−104° C.).

As shown in FIG. 10, the PCPs of Examples 3 and 4 each selectively adsorbed VdF compared to TFE. This was presumed to be caused by the fact that the deviation of the charge in TFE was symmetric and while the deviation of the charge in VdF was asymmetric.

INDUSTRIAL APPLICABILITY

According to the method of the present invention, a halogenated unsaturated carbon compound that is chemically unstable and has explosive nature such as TFE can be separated and stored in a safe manner.

The invention claimed is:

1. A porous coordination polymer comprising a halogenated unsaturated carbon compound having 2 or 3 carbon atoms stored therein, wherein
the porous coordination polymer is represented by a composition formula [$Cr_3O(OH)(bdc)_3$] where bdc is 1,4-benzenedicarboxylate, [$Ni_2(dhtp)$] where dhtp is 2,5-dihydroxyterephthalate, or [$Zr_6O_4(OH)_4(bpdc)_6$] where bpdc is 4,4'-biphenyldicarboxylate.

2. The porous coordination polymer according to claim 1, wherein
the halogenated unsaturated carbon compound is one or more compound(s) selected from the group consisting of difluoroethylene, trifluoroethylene, tetrafluoroethylene, and hexafluoropropyl ene.

3. The porous coordination polymer according to claim 1, wherein
a storage amount of the halogenated unsaturated carbon compound at a temperature of 298K and at an adsorption gas pressure of 100 kPa that is an absolute pressure is 25 to 35% by weight relative to a total of a weight of the porous coordination polymer and a weight of the halogenated unsaturated carbon compound.

4. The porous coordination polymer according to claim 1, wherein the porous coordination polymer is represented by the composition formula [$Cr_3O(OH)(bdc)_3$] where bdc is 1,4-benzenedicarboxylate.

5. The porous coordination polymer according to claim 1, wherein the porous coordination polymer is represented by the composition formula [$Ni_2(dhtp)$] where dhtp is 2,5-dihydroxyterephthalate.

6. The porous coordination polymer according to claim 1, wherein the porous coordination polymer is represented by the composition formula [$Zr_6O_4(OH)_4(bpdc)_6$] where bpdc is 4,4'-biphenyldicarboxylate.

* * * * *